United States Patent [19]

Townsend

[11] 4,140,851
[45] Feb. 20, 1979

[54] SYNTHESIS AND ANTITUMOR ACTIVITY OF 2,4,5-TRISUBSTITUTED-PYRROLO[2,3-d]-PYRIMIDINE NUCLEOSIDES

[75] Inventor: Leroy B. Townsend, Salt Lake City, Utah

[73] Assignee: The United States of America as represented by the Department of Health, Education and Welfare, Washington, D.C.

[21] Appl. No.: 853,490

[22] Filed: Nov. 21, 1977

[51] Int. Cl.$^2$ .................... C07H 17/00; C07H 19/06; A61K 31/70
[52] U.S. Cl. .................................. 536/24; 424/180; 536/26
[58] Field of Search .............................. 536/24

[56] References Cited
PUBLICATIONS

Cheng, C. S., et al., J. Am. Chem. Soc., 98:7870, (1976).
Henshaw, B. C., J. Org. Chem., 35:236, (1970).

*Primary Examiner*—Johnnie R. Brown
*Assistant Examiner*—Blondel Hazel
*Attorney, Agent, or Firm*—John S. Roberts, Jr.; Norman J. Latker; Thomas G. Ferris

[57] ABSTRACT

Certain trisubstituted pyrrolopyrimidine nucleosides are prepared from toyocamycin and have shown antitumor activity against L1210 and P388 murine leukemia. The particular compounds of interest are selected from the following structural formula:

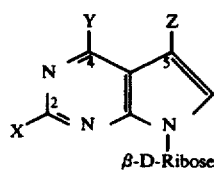

where
X is halo
Y is halo; —NH$_2$; —SH, —SR (where R is lower alkyl, benzyl); —OR (where OR is methoxy or alkoxy or where alk is C1–C6); amino (where the amino is —NH$_2$, -alkyl amino or -dialkyl amino and alkyl is C1–C6); gamma gamma dimethyl allyl amino; benzyl amino; phenyl amino; seleno
Z is CN; CXNH$_2$ where X is =O, =S, or =Se, =NH, =NHNH$_2$, =NOH. OR Z is = —CH$_2$NH$_2$, —COR=NH
Rib=β-D-ribofuranosyl Preferred members of this group of compounds are shown by the following structural formula:

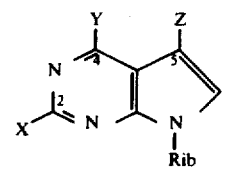

where
X is Cl
Y is Cl or NH$_2$
Z is CN, CONH$_2$, or C=NOH—NH$_2$
These compounds are further identified as NSC #145387 (Compound 5)

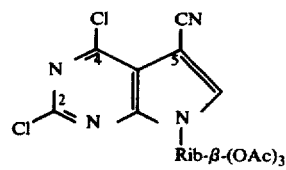

NSC #177369 (Compound 6)

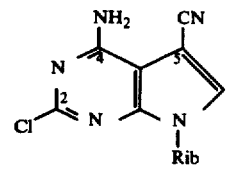

NSC #182864 (Compound 8)

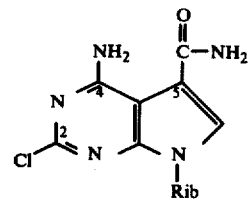

NSC #180526 (Compound 10)

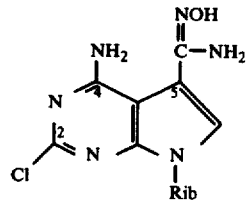

These compounds at dosages of 13 – 200 mg/kg of body weight administered every other day on the standard six-day schedule showed activity against both L1210 and P388 murine leukemia (Protocol 11, National Institutes of Health, November 11, 1972).

6 Claims, No Drawings

SYNTHESIS AND ANTITUMOR ACTIVITY OF 2,4,5-TRISUBSTITUTED-PYRROLO[2,3-d]-PYRIMIDINE NUCLEOSIDES

Certain trisubstituted pyrrolopyrimidine nucleosides are prepared from toyocamycin and have shown antitumor activity against L1210 and P388 murine leukemia. The particular compounds of interest are selected from the following structural formula:

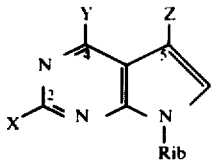

where
- X is halo
- Y is halo; —$NH_2$; —SH, —SR (where R is lower alkyl, benzyl); —OR (where OR is methoxy or alkoxy or where alk is $C_1$–$C_6$); amino (where the amino is —$NH_2$,-alkyl amino or -dialkyl amino and alkyl is $C_1$–$C_6$); gamma gamma dimethyl allyl amino; benzyl amino; phenyl amino; seleno
- Z is CN; $CXNH_2$ where X is —O, —S, or —Se, —NH, —$NHNH_2$, —NOH, —$CH_2NH_2$, —COR=NH Preferred members of this group of compounds are shown by the following structural formula:

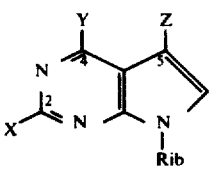

where
- X is Cl
- Y is Cl or $NH_2$
- Z is CN, $CONH_2$, or C=NOH—$NH_2$

These compounds are further identified as NSC #145387 (Compound 5)

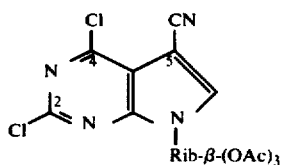

NSC #177369 (Compound 6)

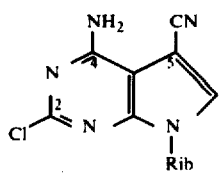

NSC #182864 (Compound 8)

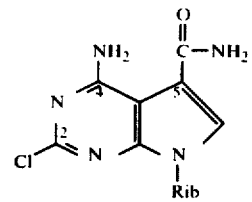

NSC #180526 (Compound 10)

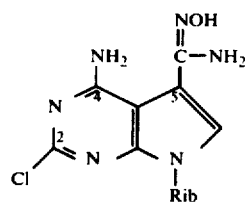

These compounds at dosages of 13 - 200 mg/kg of body weight administered every other day on the standard six-day schedule showed activity against both L1210 and P388 murine leukemia (Protocol 11, National Institutes of Health, November 11, 1972).

PRIOR ART STATEMENT

B. C. Hinshaw, O. Leonoudakis, K. H. Schram, and L. B. Townsend, "Pyrrolopyrimidine Nucleosides. Part X. Synthesis of Certain 4,5-Disubstituted 7-(β-D-Ribofuranosyl)pyrrolo[2,3-d]pyrimidines Related to Toyocamycin and Sangivamycin," J. Chem. Soc., Perkin Transactions I, 1975, pp. 1248–1253.

K. H. Schram and L. B. Townsend, "Pyrrolopyrimidine Nucleosides. Part XI. Influence of Amino-groups at C-4 and C-6 or an Amino-group at C-6 on the Reactivity of a 5-Cyanogroup in Pyrrolo[2,3-d]pyrimidines Nucleosides," J. Chem. Soc., Perkin Transactions I, 1975, pp. 1253–1257.

B. C. Hinshaw, J. F. Gerster, R. K. Robins, and L. B. Townsend, "Pyrrolopyrimidine Nucleosides. V. A Study on the Relative Chemical Reactivity of the 5-Cyano Group of the Nucleoside Antibiotic Toyocamycin and Desaminotoyocamycin. The Synthesis of Analogs of Sangivamycin," J. Org. Chem., 35:236 (1970).

R. L. Tolman, R. K. Robins, and L. B. Townsend, "Pyrrolopyrimidine Nucleosides VII. A Study on Electrophilic and Nucleophilic Substitution at Position Six of Certain Pyrrolo[2,3-d]pyrimidine Nucleosides," J. Heterocyclic Chem., 8:702 (1971).

C. S. Cheng, B. C. Hinshaw, R. P. Panzica, and L. B. Townsend, "Synthesis of 2-Amino-5-cyano-7-(B-D-ribofuranosyl)pyrrolo[2,3-d]pyrimidin-4-one. An Important Precursor for the Synthesis of Nucleoside Q and Q*," J. Am. Chem. Soc., 98:7870 (1976).

The following diagramatic reaction schemes are described post in the text.

REACTION SCHEME 1
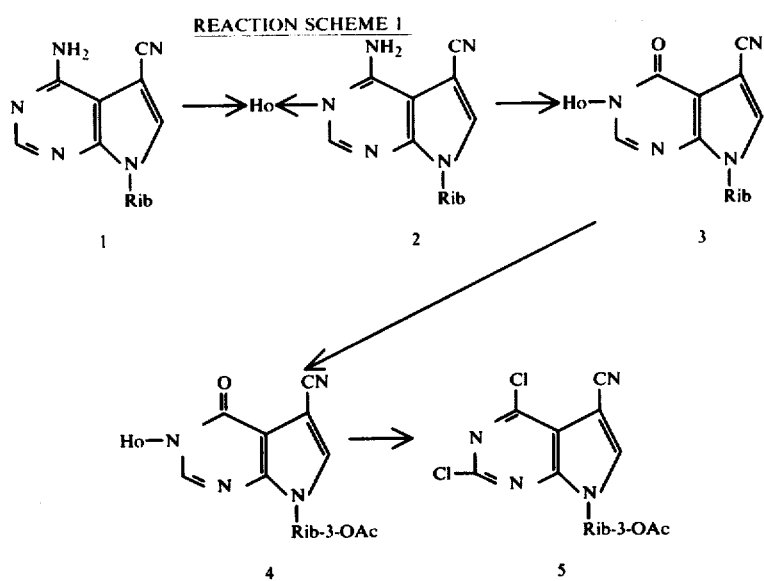
REACTION SCHEME 2
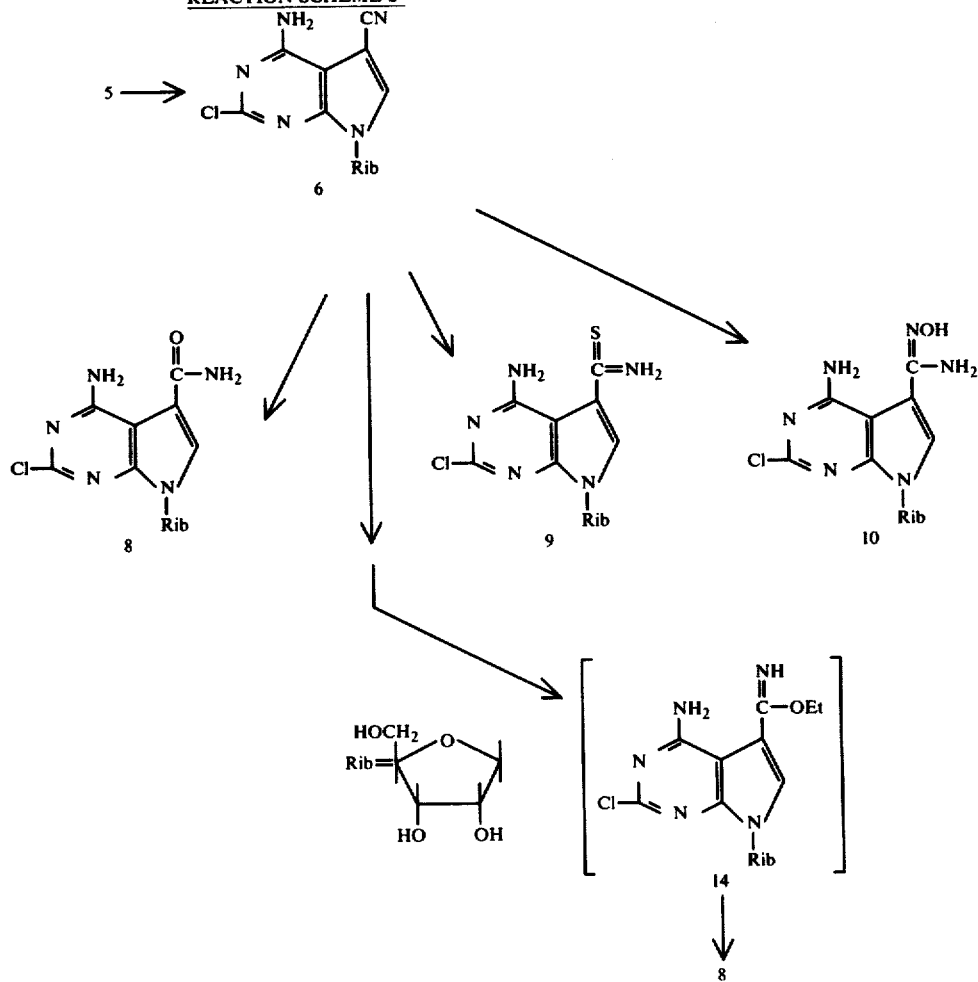
The present reaction scheme applied to the most preferred compounds proceeds from toyocamycin 1 which involves especially a consideration of Compound 5 which may by nucleophilic displacement of halogen at C-4 as by amino to produce Compound 6. Also important to the reaction scheme is the nucleophilic addition to a cyano group at C-5 of Compound 6 which produces Compound 8. Studies have shown with respect to Compound 5 having the 4-chloro-5-cyano groups and succeeding compounds such as 6 and 8 that the initial reaction is nucleophilic displacement of the 4-chloro group as in 6 followed by addition to the nitrile function as in 8 producing the 4-amino-5-carboxamide.

Referring to the reaction scheme above, toyocamycin (1) was converted to toyocamycin-3-N-oxide (2) by treatment with m-chlorobenzoic acid. Deamination of 2 gave 5-cyano-3-N-hydroxy-7-($\beta$-D-ribofuranosyl)pyrrolo[2,3-d]pyrimidin-4 one (3) and this procedure was accomplished using sodium nitrite and glacial acetic acid. Acetylation of 3 using pyrimidine and acetic anhydride gave 4, which was chlorinated with phosphorous oxychloride to produce 5-cyano-2,4-dichloro-7-(2,3,5-tri-O-acetyl-$\beta$-D-ribofuranosyl)pyrrolo[2,3-d]pyrimidine (5). The pmr spectrum of 5 showed a peak at $\delta$ 8.15 which was assigned to the C-6 proton peaks for the carbohydrate protons between $\delta$3.5 and $\delta$4, and peaks for the acetyl protons (9H) in the $\delta$ 2.1 region. An ir spectrum of 5 showed a strong absorbance in the 2210 cm$^{-1}$ region and confirmed that no modification of the nitrile group had occurred during the above transformations. This dichloro compound 5 was important in the production of subsequent compounds and specially here was used to prepare 2-chloro-toyocamycin (6) as follows.

Treatment of 5 with liquid ammonia in a sealed reaction vessel for 12 hours at room temperature afforded nucleoside material which was 4-amino-2-chloro-5-cyano-7-($\beta$-D-ribofuranosyl)pyrrolo[2,3-d]pyrimidine (2-chlorotoyocamycin, 6). In structure proof of 6, a pmr spectrum of 6 showed absorbances for the aromatic proton (1H, S, $\delta$ 8.48), the carbohydrate protons (8H, $\delta$ 3.5- $\delta$ 5), the anomeric proton (1H, d. $\delta$ 6.07) and a single amino group (2H, broad, $\delta$ 7.37). This was the expected and desired result since the introduction of one electron donating group (NH$_2$) would increase the electron density at the second halogen and make nucleophilic displacement of the second halogen more difficult. Additionally, an ir spectrum of 6 showed a strong absorbance at 2210 cm$^{-1}$ assigned to the nitrile moiety which precluded the possibility of amidine formation. Thus, it was found that the reaction of 5 with liquid ammonia at room temperature effected displacement of only one of the two chloro groups and also removed the acetyl blocking groups to produce compound 6.

The structure for 8 was established in the following manner. Conversion of 6 to 4-amino-2-chloro-7-($\beta$-D-ribofuranosyl)-pyrrolo[2,3-d]pyrimidine-5-carboxamide (2-chlorosangivamycin, 8) was achieved using con:ammonium hydroxide and hydrogen peroxide. The ir spectrum of 8 displayed no absorbance for a nitrile group and confirmed that oxidation to 8 had occurred. The pmr spectrum of 8 showed, in addition to the carbohydrate peaks, absorbances for an aromatic proton, the 4-amino group, and the carboxamide amino group.

The reaction of 6 → 8 is a reaction which was found to be a good measure of the susceptibility of the nitrile group toward nucleophilic addition by the addition of solid hydroxylamine to nitrile functions. The reaction of 6 with hydroxylamine in ethanol afforded 4-amino-2-chloro-7-($\beta$-D-ribofuranosyl)pyrrolo[2,3-d]pyrimidine-5-carboxamidoxime (10). An ir spectrum confirmed that addition to the nitrile group had occurred and a pmr spectrum showed absorbances for the carboxamidoxime ($\delta$9.7 for -NOH and $\delta$6.1 for -NH$_2$), the C-4 amino group ($\delta$ 7.8), the C-6 protom ($\delta$ 7.9) and the carbohydrate protons. The addition of hydroxylamine to 6 occurred approximately four times faster than the corresponding addition to 1 (0.5 hr vs 2 hr). It would appear that the 2-chloro group does activate the cyano moiety of 6 toward nucleophilic addition since by comparison with corresponding nucleosides without the presence of 2-chloro proceeded at a much slower reaction rate (0.5 hr vs 2 hr).

It is noted that the reaction of 5 with ammonia at room temperature affords 6 in moderate yields and nucleophilic displacement is selective for the chloro group at C-4. However, at elevation temperatures (100° for ammonia or 65° for sodium methoxide) the selectivity is lost and a multitude of products are formed.

GENERAL EXPERIMENTAL DATA

In this process experimentally, melting points were determined with a Thomas-Hoover melting point apparatus and are uncorrected. Thin layer chromatography was performed using 0.25 mm thick SilicAR 7GF plates with the following solvent system: (n-PrOH/EtOAc/-HZO [1/4/2: v/v/v] upper phase). PMR spectra were obtained on a Varian A-56/60 instrument using tetramethylsilane as an internal standard. Infrared spectra were determined on a Beckman IR-5A using pressed potassium bromide pellets.

| ULTRAVIOLET ABSORPTION SPECTRA OF CERTAIN PYRROLOPYRIMIDINE NUCLEOSIDES | | | | | | |
|---|---|---|---|---|---|---|
| | pH 1 | | MeOH | | pH 11 | |
| Compound | $\lambda_{max}$ | $\epsilon^a$ | $\lambda_{max}$ | $\epsilon$ | $\lambda_{max}$ | $\epsilon$ |
| 5-Cyano-2,4-dichloro-7-(2,3,5-tri-O-acetyl-$\beta$-D-ribofuranosyl)pyrrolo-[2,3-d]pyrimidine (5) | | | 285 | 6.13 | | |
| 4-Amino-2-chloro-5-cyano-7-($\beta$-D-ribofuranosyl)pyrrolo[2,3-d]pyrimidine (2-chlorotoyocamycin, 6) | 278 | 19.5 | 280 | 20.1 | 278 | 20.0 |
| 4-Amino-2-chloro-7-($\beta$-D-ribofuranosyl)pyrrolo[2,3-d]pyrimidine-5-carboxamide (2-chlorosangivamycin, 8) | 280 | 16.1 | 281 | 17.5 | 280 | 17.2 |
| 4-Amino-2-chloro-7-($\beta$-D-ribofuranosyl)pyrrolo-[2,3-d]pyrimidine-5- | 278 | 13.6 | 279 | 11.8 | 279 (238)$^b$ | 12.3 15.2 |

| | ULTRAVIOLET ABSORPTION SPECTRA OF CERTAIN PYRROLOPYRIMIDINE NUCLEOSIDES | | | | | |
|---|---|---|---|---|---|---|
| | pH 1 | | MeOH | | pH 11 | |
| Compound | $\lambda_{max}$ | $\epsilon^a$ | $\lambda_{max}$ | $\epsilon$ | $\lambda_{max}$ | $\epsilon$ |
| carboxamidoxime (10) | | | | | | |

$^a \epsilon \cdot 10^{-3}$
$^b$() shoulder

EXAMPLE 1

4-Amino-5-cyano-7-($\beta$-D-ribofuranosyl)pyrrolo[2,3-d]pyrimidine-3-N-oxide (Toyocamycin-3-N-oxide) (2)

Toyocamycin (1, 15 g) and m-chloroperbenzoic acid (22.5 g) were suspended in 300 mls of glacial acetic acid and the mixture was magnetically stirred and heated at 62-64° in an oil bath for 2 hrs. The solution was then poured into one 1 of ice water, the resulting mixture was filtered and the filter cake was washed with 250 ml of water. The filtrate was evaporated to dryness in vacuo and the residue was stirred overnight with 750 ml of ethylacetate. The mixture was filtered and the filter cake was washed with 250 ml of ethylacetate and air dried. The solid was then dissolved in 500 ml of boiling water and allowed to stand at 5° C. for 12 hr. The white crystalline solid was collected by filtration, washed with 100 ml of water and dried in a vacuum oven at 100° for 2 hrs over drierite to yield 10 g (63%) of 2, mp > 270° C. dec.

Anal. Calcd for $C_{12}H_{13}N_5O_5$: C, 47.00; H, 4.26; N, 22.80. Found: C, 47.50; H, 4.52; N, 22.89.

EXAMPLE 2

5-Cyano-3-N-hydroxy-7-($\beta$-D-ribofuranosyl)pyrrolo[2,3-d]-pyrimidine-4-one (3)

Toyocamycin-3-N-oxide (2, 8 g) and sodium nitrite (7 g) were added to 80 ml of dimethylformamide containing 20 ml of 15% acetic acid in water. The mixture was heated on a steam bath for 2 hr and poured into 800 mls of well stirred ethyl acetate. After 2-3 hr the ethyl acetate was decanted and the residue was dissolved in 250 ml methanol. After cooling at 5° for 12 hr the solid was collected by filtration, dissolved in 50 ml of warm water and neutralized to pH 5 with amberlite IR-120 H (C.P.) [H+ form]. The solution was filtered rapidly from the resin, the resin was washed with 20 ml of boiling water and the filtrate was allowed to stand at 5° for 12 hr. The white crystalline solid was collected by filtration, washed with 25 ml of cold water and dried in a vacuum oven at 100° for 12 hr over drierite to yield 4.25 g (53%) of 3, mp 229-231°. For analysis, a small sample was recrystallized from a minimum amount of distilled water and dried in an Abderhalden apparatus over drierite in vacuo at the temperature of refluxing toluene for 2 hr, mp 230-232° C.

Anal. Calcd for $C_{12}H_{12}N_4O_6$: C, 46.74; H, 3.92; N, 18.2. Found: C, 46.65; H, 4.35; N, 18.51.

EXAMPLE 3

5-Cyano-3-N-hydroxy-7-(2,3,5-tri-O-acetyl-$\beta$-D-ribofuranosyl)-pyrrolo[2,3-d]pyrimidin-4-one (4)

5-Cyano-3-N-hydroxy-7-($\beta$-D-ribofuranosyl)pyrrolo[2,3-d]pyrimidin-4-one was dissolved in a mixture of 50 ml of pyridine and 25 ml of acetic anhydride. The solution was allowed to stand at room temperature for 5 hr and evaporated in vacuo to a thick oil. This residue was triturated with 100 ml of ethanol and the mixture was evaporated in vacuo to a solid foam which was again triturated with 100 ml of ethanol and evaporated in vacuo to dryness. The resulting foam was heated at reflux temperature with 100 ml of methanol for 1 hr. The methanol was removed in vacuo and an additional 100 ml of methanol was added and removed in vacuo to furnish a solid foam which was used without further purification.

EXAMPLE 4

5-Cyano-2,4-dichloro-7-(2,3,5-tri-O-acetyl-$\beta$-D-ribofuranosyl)-pyrrolo[2,3-d]pyrimidine (5)

5-Cyano-3-N-hydorxy-7-(2,3,5-tri-O-acetyl-$\beta$-D-ribofuranosyl)pyrrolo[2,3-d]pyrimidin-4-one (4, 4.00 g) was added to 100 ml of $PoCl_3$ and 4 ml of 2,6-dimethylpyridine and the mixture was heated at reflux temperature for 4 hr. The solution was then evaporated in vacuo to ~$\frac{1}{2}$ volume and the residue was poured cautiously onto excess crushed ice with vigorous stirring. The mixture was extracted with 3 × 250 ml of methylene chloride and the combined methylene chloride extracts were washed with 2 × 250 ml of water. The methylene chloride solution was then dried over anhydrous $MgSO_4$ and the mixture, after the addition of decolorizing carbon, was filtered through a celite pad and the pad was washed with 250 ml of methylene chloride. The filtrate was evaporated to ~100 ml in vacuo and 20 ml of Baker silica gel was added. The mixture was evaporated to dryness in vacuo and the solid was placed on the top of a 2" nylon dry column packed with 100 g of Baker silica gel plus .4% phosphor added and the product was eluted with 200 ml of ethyl acetate. The ethyl acetate eluent was evaporated in vacuo to a cream-colored solid foam which was dried in vacuo in a dessicator for 12 hr to yield 2.50 g (67%) of 5, mp 70-75°.

Anal. Calcd for $C_{18}H_{16}N_4O_7Cl_2$: C, 45.86; H, 3.42; N, 11.89. Found: C, 46.19; H, 3.46; N, 11.90.

EXAMPLE 5

4-Amino-2-chloro-5-cyano-7-($\beta$-D-ribofuranosyl)pyrrolo[2,3-d]-pyrimidine (2-chlorotoyocamycin, 6)

5-Cyano-2,4-dichloro-7-(2,3,5-tri-O-acetyl-$\beta$-D-ribofuranosyl)pyrrolo[2,3-d]pyrimidine (5, 2.85 g) was covered with 50 ml of liquid ammonia and the solution was allowed to stand at room temperature for 12 hr while sealed in a steel vessel. The excess ammonia was allowed to evaporate and the residue was triturated with 50 ml of cold water. The water insoluble solid was collected by filtration, washed with 10 ml of water and dissolved in a minimum amount of boiling methanol. The methanol solution was then concentrated to ~100 ml or until the product began to crystallize. The solution was then allowed to stand at −5° for 12 hr. The white to light tan crystalline solid was collected by filtration, washed with 15 ml of methanol and dried in a vacuum oven for 2 hr at 100° over drierite to yield 1.00 g (51%) of 6, mp 258-260° dec.

Anal. Calcd for $C_{12}H_{12}N_5O_4Cl \cdot \frac{1}{2}$ MeOH verified by pmr. C, 43.95; H, 4.09; N, 20.46. Found: C, 44.18; H, 4.08; N, 20.49.

EXAMPLE 6

2-Chloro-5-cyano-4-methoxy-7-($\beta$-D-ribofuranosyl)-pyrrolo-[2,3-d]pyrimidine (7)

5-Cyano-2,4-dichloro-7-(2,3,5-tri-O-acetyl-$\beta$-D-ribofuranosyl)pyrrolo[2,3-d]pyrimidine (5, 400 mg) was dissolved in 40 ml of methanol containing 200 mg of sodium methoxide. The solution was stirred at room temperature for 1 hr and neutralized to pH 7 with Dowex 50W-X 12 ($H^{30}$) resin. The resin was filtered and the solvent was evaporated to dryness in vacuo. The residue was dissolved in water, treated with decolorizing carbon, filtered and the product slowly crystallized under an air stream. The solid was recrystallized from ethanol-water to yield 100 mg of 7, mp 194–195°. The analytical sample was dried in an Abderhalden apparatus in vacuo for 2 hr. at 110° (mp unchanged).

Anal. Calcd for $C_{13}H_{13}N_4O_5Cl \cdot \frac{1}{2} H_2O$ verified by pmr, C, 44.66; H, 4.03; N, 16.00. Found: C, 44.09; H, 4.52; N, 16.50.

EXAMPLE 7

4-Amino-2-chloro-7-($\beta$-D-ribofuranosyl)pyrrolo[2,3-d]-pyrimidine-5-carboxamide (2-chlorosangivamycin, 8)

2-Chlorotoyocamycin (6, 200 mg) was suspended in 40 ml of conc. ammonium hydroxide and 4 ml of 30% hydrogen peroxide were added. The mixture was stirred at room temperature for 2 hr and 2 more ml of 30% hydrogen peroxide were added. Stirring at room temperature was continued for 2 more hours and 2 more ml of 30% hydrogen peroxide were added and the solution was stirred at room temperature for an additional 12 hr. One more ml of hydrogen peroxide was added and stirring at room temperature was continued for an additional hour and the solution was evaporated to dryness in vacuo. The residue was coevaporated first with 40 ml of ethanol and then 40 ml of acetone. The residue was suspended in 50 ml of chloroform, the solid was collected by filtration, washed with 25 ml of chloroform and air dried. The product was then crystallized from 10 ml of absolute ethanol to yield, after drying the sample in an Abderhalden apparatus for 2 hr in vacuo at 110°, 100 mg (47%) of 8, mp 175° dec.

Anal. Calcd for $C_{12}H_{14}N_5O_5Cl$: C, 41.95; H, 4.07; N, 20.39. Found: C, 41.96; H, 4.07; N, 20.42.

EXAMPLE 8

4-Amino-2-chloro-7-($\beta$-D-ribofuranosyl)pyrrolo[2,3-d]-pyrimidine-5-thiocarboxamide (2-chlorothiosangivamycin, 9)

2-Chlorotoyocamycin (6, 500 mg) was added to 65 ml of dry pyridine containing 1 ml of triethylamine. The solution was magnetically stirred and saturated with dry hydrogen sulfide gas for 30 min. This solution was then stirred at room temperature for 5 hr during which time it was again saturated with hydrogen sulfide every 2 hr for 10 min and then stirred at room temperature for 12 hr. The solvent was removed in vacuo and the residue was coevaporated first with 50 ml of water and then 50 ml of ethanol. The residue was extracted with 50 ml of acetone, the acetone insoluble material was collected by filtration, washed with ~25 ml of acetone and the filtrate was evaporated in vacuo to a solid foam. Recrystallization from methanol-water gave, after drying for 2 hr in an Abderhalden apparatus in vacuo over drierite at 100°, 350 mg (67%) of 9, mp 185° dec.

Anal. Calcd for $C_{12}H_{14}N_5O_4SCl \cdot \frac{1}{2} H_2O$ (verified by pmr): C, 39.02; H, 4.07; N, 18.96. Found: C, 39.01; H, 4.05; N, 18.91.

EXAMPLE 9

4-Amino-2-chloro-7-($\beta$-D-ribofuranosyl)pyrrolo[2,3-d]pyrimidine-5-carboxamidoxime (10)

2-Chlorotoyocamycin (6, 250 mg) and solid hydroxylamine (250 mg) were added to 20 ml of absolute ethanol and the mixture was heated at reflux temperature for 30 min. The solution was allowed to stand at −10° for 24 hr and the solid was collected by filtration, washed with 10 ml of ice cold ethanol and recrystallized from water to yield 200 mg (76%) of 10, mp 170° dec.

Anal. Calcd for $C_{12}H_{15}N_6O_5Cl$: C, 40.10; H, 4.18; N, 23.40. Found: C, 40.10; H, 4.42; N, 23.32

EXAMPLE 10

In a further experiment an imino ether compound (14 in the reaction scheme) was formed but quickly hydrolyzed to revert to 8. This imino ether 14 is a compound with O-alk where alk is methyl, ethyl, propyl, butyl, or $C_1$–$C_6$.

CANCER SCREENING INFORMATION

Compound 5 against L1210 murine leukemia proved to be not especially active.

Compound 6 in dosages of 3.12 - 50 mg/kg of body weight against P388 murine leukemia showed a majority of values for T/C in the range 140–166 with satisfactory toxicity on a six-day schedule. Also, against L1210, this compound was not as active where dosages were in the range 12.5 - 200 mg/kg of body weight gave T/C values 98 - 128, thus being marginal for L1210.

Compound 8 in dosages of 50 - 100 mg/kg of body weight showed activity against L1210 murine leukemia of values for T/C in the range 148-165 with satisfactory toxicity.

Compound 10 against L1210 murine leukemia in dosages of 100 - 200 mg/kg of body weight was marginally active.

I claim:

1. A pyrrolopyrimidine compound represented by the following structural formula:

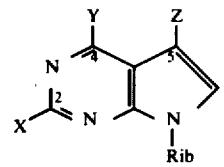

where

X is halo

Y is halo; —$NH_2$; —SH, —SR (where R is lower alkyl, benzyl); —OR (where OR is methoxy or alkoxy or where alk is Cl-C6); amino (where the amino is —$NH_2$, -alkyl amino or -dialkyl amino and alkyl is C1-C6); gamma gamma dimethyl allyl amino; benzyl amino; phenyl amino; seleno Z is CN; $CXNH_2$ where X is =O, =S, or =Se, =NH, =$NHNH_2$, =NOH or Z is —$CH_2NH_2$, —COR=NH Rib is B-D-ribofuranosyl.

2. A pyrrolopyrimidine compound selected from the group consisting of (a) 5-cyano-2,4-dichloro-7-(-2,3,5-tri-O-acetyl-β-D-ribofuranosyl)pyrrolo[2,3-d]pyrimidine, (b) 4-amino-2-chloro-5-cyano-7-(β-D-ribofuranosyl)pyrrolo[2,3-d]pyrimidine, (c) 4-amino-2-chloro-7-(β-D-ribofuranosyl)-pyrrolo[2,3-d]pyrimidine-5-carboxamide, and (d) 4-amino-2-chloro-7-(β-D-ribofuranosyl)pyrrolo[2,3-d]pyrimidine-5-carboxamidoxime.

3. The compound according to claim 2 wherein said compound is 5-cyano-2,4-dichloro-7-(-2,3,5-tri-O-acetyl-β-D-ribofuranosyl)pyrrolo[2,3-d]pyrimidine.

4. The compound according to claim 2 wherein said compound is 4-amino-2-chloro-5-cyano-7-(β-D-ribofuranosyl)-pyrrolo[2,3-d]pyrimidine.

5. The compound according to claim 2 wherein said compound is 4-amino-2-chloro-7-(β-D-ribofuranosyl)-pyrrolo-[2,3-d]pyrimidine-5-carboxamide.

6. The compound according to claim 2 wherein said compound is 4-amino-2-chloro-7-(β-D-ribofuranosyl)-pyrrolo-[2,3-d]pyrimidine-5-carboxamidoxime.

* * * * *